(12) United States Patent
Faryniarz et al.

(10) Patent No.: US 7,867,522 B2
(45) Date of Patent: Jan. 11, 2011

(54) METHOD OF WOUND/BURN HEALING USING COPPER-ZINC COMPOSITIONS

(75) Inventors: Joseph R. Faryniarz, Middlebury, CT (US); Jose E. Ramirez, Trumbull, CT (US)

(73) Assignee: JR Chem, LLC, Key West, FL (US)

( * ) Notice: Subject to any disclaimer, the term of this patent is extended or adjusted under 35 U.S.C. 154(b) by 0 days.

(21) Appl. No.: 11/648,278

(22) Filed: Dec. 29, 2006

(65) Prior Publication Data

US 2008/0081077 A1 Apr. 3, 2008

Related U.S. Application Data

(60) Provisional application No. 60/848,616, filed on Sep. 28, 2006.

(51) Int. Cl.
  *A01N 59/00* (2006.01)
  *A01N 59/20* (2006.01)
  *A01N 59/16* (2006.01)
  *A61K 33/00* (2006.01)
  *A61K 33/34* (2006.01)
  *A61K 33/32* (2006.01)

(52) U.S. Cl. .................. 424/630; 424/600; 424/641
(58) Field of Classification Search .................. 424/600, 424/630, 641
See application file for complete search history.

(56) References Cited

U.S. PATENT DOCUMENTS

| | | |
|---|---|---|
| 46,494 A | 2/1865 | Pike |
| 51,868 A | 1/1866 | Schuster |
| 55,889 A | 6/1866 | Noll |
| 81,008 A | 8/1868 | Roemheld |
| 81,711 A | 9/1868 | Van Wagenen |
| 87,343 A | 3/1869 | Johnson |
| 88,973 A | 4/1869 | McDowell |
| 92,065 A | 6/1869 | Lighthall |
| 93,300 A | 8/1869 | Hall et al. |
| 116,875 A | 7/1871 | Shannon |
| 124,751 A | 3/1872 | Lauer |
| 127,925 A | 6/1872 | Roskopf |
| 128,385 A | 6/1872 | Goffinet |
| 140,768 A | 7/1873 | Fisher |
| 143,133 A | 9/1873 | Fehr |
| 145,749 A | 12/1873 | Pawlewski et al. |
| 149,857 A | 4/1874 | Halpen |
| 171,875 A | 1/1876 | Sievers |
| 173,607 A | 2/1876 | Fehr |
| 209,331 A | 10/1878 | Littleton |
| 229,014 A | 6/1880 | Sharetts |
| 232,807 A | 10/1880 | Dennett |
| 238,015 A | 2/1881 | Yater |
| 264,783 A | 9/1882 | Squier |
| 277,221 A | 5/1883 | Buse |
| 284,335 A | 9/1883 | Scott |
| 318,468 A | 5/1885 | Haley |
| 320,836 A | 6/1885 | Bisaillon |
| 411,657 A | 9/1889 | Grosbety |
| 415,208 A | 11/1889 | Johson |
| 430,048 A | 6/1890 | Wainwright |
| 432,611 A | 7/1890 | Hall |
| 627,296 A | 6/1899 | Camnitzer |
| 928,539 A | 7/1909 | Pucciarelli |
| 944,738 A | 12/1909 | Loose |
| 992,937 A | 5/1911 | Brodbeck et al. |
| 1,059,841 A | 4/1913 | Crookes |
| 1,086,900 A | 2/1914 | David |
| 1,332,190 A | 2/1920 | Hull |
| 1,411,577 A | 4/1922 | Mullins et al. |
| 1,488,097 A | 3/1924 | Creger |
| 1,584,173 A | 5/1926 | Holzapfel |
| 1,593,485 A | 7/1926 | Crosnier |
| 1,627,963 A | 5/1927 | Fuller |
| 1,809,082 A | 6/1931 | Urkov et al. |
| 1,908,176 A | 5/1933 | Osterberg |
| 1,947,568 A | 2/1934 | Noonan |
| 1,949,797 A | 3/1934 | Kaufmann |
| 1,982,148 A | 11/1934 | Zimbron, Jr. |
| 2,002,829 A | 5/1935 | Osterberg |
| 2,054,989 A | 9/1936 | Moore |

(Continued)

FOREIGN PATENT DOCUMENTS

JP  2001039809  2/2001

(Continued)

OTHER PUBLICATIONS

Ruiz-Pérez, et al.. "Malonic Acid: a multi-modal bridging ligand for new architectures and properties on molecule-based magnets" *Polyhedron* 2003, accepted.

(Continued)

*Primary Examiner*—Johann R Richter
*Assistant Examiner*—Luke E Karpinski
(74) *Attorney, Agent, or Firm*—Carter, DeLuca, Farrell & Schmidt, LLP

(57) ABSTRACT

Composition and methods for alleviating or eliminating wounds and/burns by providing an effective amount of one or more copper, zinc and copper-zinc compositions are disclosed. Treatment is accomplished through the use of topical compositions containing one or more copper or zinc salts and/or copper-zinc compounds or complexes, particularly copper-zinc malonate active ingredient.

26 Claims, No Drawings

U.S. PATENT DOCUMENTS

| | | |
|---|---|---|
| 2,087,162 A | 7/1937 | Moore |
| 2,095,092 A | 10/1937 | Barton |
| 2,114,490 A | 4/1938 | Harris |
| 2,129,836 A | 9/1938 | Goodman |
| 2,153,653 A | 4/1939 | Stux |
| 2,194,218 A | 3/1940 | Thurstan |
| 2,223,142 A | 11/1940 | Weirich |
| 2,241,331 A | 5/1941 | Shelton |
| 2,254,636 A | 9/1941 | Vangunten |
| 2,267,739 A | 12/1941 | Kemppe |
| 2,289,125 A | 7/1942 | Keil |
| 2,299,604 A | 10/1942 | Weirich |
| 2,344,830 A | 3/1944 | Mohs |
| 2,361,161 A | 10/1944 | Anderson |
| 2,370,561 A | 2/1945 | Mecca |
| 2,372,807 A | 4/1945 | Brown |
| 2,420,271 A | 5/1947 | Travis et al. |
| 2,420,389 A | 5/1947 | Travis et al. |
| 2,469,228 A | 5/1949 | Gertler |
| 2,527,686 A | 10/1950 | Sandberg |
| 2,556,567 A | 6/1951 | Wright |
| 2,602,039 A | 7/1952 | Wershaw |
| 2,649,398 A | 8/1953 | Wright et al. |
| 2,652,355 A | 9/1953 | Ercoli et al. |
| 2,673,364 A | 3/1954 | Diveley |
| 2,703,777 A | 3/1955 | Feinstein et al. |
| 2,736,681 A | 2/1956 | Tishler |
| 2,748,781 A | 6/1956 | Collat |
| 2,838,440 A | 6/1958 | Thurmon |
| 2,843,522 A | 7/1958 | Mahon |
| 2,846,322 A | 8/1958 | Buchalter |
| 2,870,150 A | 1/1959 | Wright et al. |
| 2,870,151 A | 1/1959 | Wright et al. |
| 2,872,372 A | 2/1959 | Hull |
| 2,991,224 A | 7/1961 | Bell |
| 3,013,883 A | 12/1961 | Welcker et al. |
| 3,033,755 A | 5/1962 | Jacobi |
| 3,035,988 A | 5/1962 | Cohen |
| 3,084,105 A | 4/1963 | Slodki |
| 3,137,622 A | 6/1964 | Mueller et al. |
| 3,146,168 A | 8/1964 | Battista |
| 3,164,523 A | 1/1965 | Fox et al. |
| 3,184,376 A | 5/1965 | Degoli |
| 3,210,248 A | 10/1965 | Feldmann et al. |
| 3,215,599 A | 11/1965 | Thau et al. |
| 3,255,079 A | 6/1966 | Schroeder et al. |
| 3,290,218 A | 12/1966 | de Jong |
| 3,317,372 A | 5/1967 | Hart |
| 3,366,114 A | 1/1968 | Kanter |
| 3,590,123 A | 6/1971 | Melloh et al. |
| 3,749,772 A | 7/1973 | Cardarelli et al. |
| 3,821,370 A | 6/1974 | Tenta |
| 3,821,371 A | 6/1974 | Battista |
| 3,826,845 A | 7/1974 | Suyama et al. |
| 3,856,941 A | 12/1974 | Turner |
| 3,896,238 A | 7/1975 | Smith |
| 3,903,268 A | 9/1975 | Balassa |
| 3,949,072 A | 4/1976 | Tenta |
| 4,048,300 A | 9/1977 | Tomlinson et al. |
| 4,100,269 A | 7/1978 | Pader |
| 4,138,477 A | 2/1979 | Gaffar |
| 4,146,607 A | 3/1979 | Ritchey |
| 4,160,821 A | 7/1979 | Sipos |
| 4,161,526 A | 7/1979 | Gorman |
| 4,166,108 A | 8/1979 | Brown et al. |
| 4,226,851 A | 10/1980 | Sompayrac |
| 4,226,889 A | 10/1980 | Yuhas |
| 4,229,430 A | 10/1980 | Fahim et al. |
| 4,229,437 A | 10/1980 | Likens et al. |
| 4,255,418 A | 3/1981 | Bailey |
| 4,273,763 A | 6/1981 | Horrobin |
| 4,285,967 A | 8/1981 | Gubernick et al. |
| 4,291,025 A | 9/1981 | Pellico |
| 4,298,601 A | 11/1981 | Howard |
| 4,302,447 A | 11/1981 | Horrobin |
| 4,309,989 A | 1/1982 | Fahim |
| 4,310,516 A | 1/1982 | Chang et al. |
| 4,315,916 A | 2/1982 | Likens et al. |
| 4,322,400 A | 3/1982 | Yuhas |
| 4,330,527 A | 5/1982 | Arima et al. |
| 4,331,653 A | 5/1982 | Brown et al. |
| 4,335,110 A | 6/1982 | Collins |
| 4,349,536 A | 9/1982 | Hausler |
| 4,372,296 A | 2/1983 | Fahim |
| 4,375,968 A | 3/1983 | Manhart |
| 4,376,115 A | 3/1983 | McCrorey |
| 4,395,398 A | 7/1983 | Yamamoto |
| 4,406,881 A | 9/1983 | Ladanyi |
| 4,428,933 A | 1/1984 | King |
| 4,430,324 A | 2/1984 | Viccaro |
| 4,444,755 A | 4/1984 | Horrobin |
| 4,465,666 A | 8/1984 | Lukas et al. |
| 4,469,684 A | 9/1984 | Huggins et al. |
| 4,477,439 A | 10/1984 | D'Alelio |
| 4,486,488 A | 12/1984 | Pietsch et al. |
| 4,503,037 A | 3/1985 | Szijjarto et al. |
| 4,512,978 A | 4/1985 | Inwood |
| 4,515,779 A | 5/1985 | Elliott |
| 4,522,806 A | 6/1985 | Muhlemann et al. |
| 4,568,540 A | 2/1986 | Asano et al. |
| 4,604,234 A | 8/1986 | Fujii et al. |
| 4,606,920 A | 8/1986 | Walter |
| 4,647,452 A | 3/1987 | Ritchey et al. |
| 4,654,213 A | 3/1987 | Ramirez et al. |
| 4,661,354 A | 4/1987 | Finnerty |
| 4,665,054 A | 5/1987 | Pickart |
| 4,678,664 A | 7/1987 | Schmolka |
| 4,683,133 A | 7/1987 | Southard |
| 4,713,242 A | 12/1987 | Trenzeluk |
| 4,760,051 A | 7/1988 | Pickart |
| 4,762,715 A | 8/1988 | Lukas et al. |
| 4,767,753 A | 8/1988 | Pickart |
| 4,810,693 A | 3/1989 | Pickart |
| 4,816,254 A | 3/1989 | Moss |
| 4,847,083 A | 7/1989 | Clark |
| 4,849,211 A | 7/1989 | Schrauzer |
| 4,855,138 A | 8/1989 | Trenzeluk |
| 4,863,897 A | 9/1989 | Dede et al. |
| 4,863,987 A | 9/1989 | Hoshino et al. |
| 4,874,361 A | 10/1989 | Obagi |
| 4,877,770 A | 10/1989 | Pickart |
| 4,895,727 A | 1/1990 | Allen |
| 4,911,932 A | 3/1990 | Clum et al. |
| 4,937,230 A | 6/1990 | Pickart |
| 4,938,969 A | 7/1990 | Schinitsky et al. |
| 4,956,354 A | 9/1990 | Gutierrez |
| RE33,512 E | 1/1991 | Ramirez et al. |
| 4,992,259 A | 2/1991 | Schiraldi et al. |
| 5,000,944 A | 3/1991 | Prencipe et al. |
| 5,023,237 A | 6/1991 | Pickart |
| 5,059,588 A | 10/1991 | Pickart |
| 5,075,469 A | 12/1991 | Chevion |
| 5,079,010 A | 1/1992 | Natterer |
| 5,091,171 A | 2/1992 | Yu et al. |
| 5,091,193 A | 2/1992 | Enjolras et al. |
| 5,093,099 A | 3/1992 | Haishi et al. |
| 5,104,644 A | 4/1992 | Douglas |
| 5,118,665 A | 6/1992 | Pickart |
| 5,120,831 A | 6/1992 | Pickart |
| 5,135,913 A | 8/1992 | Pickart |
| 5,145,838 A | 9/1992 | Pickart |
| 5,154,932 A | 10/1992 | Burba, III et al. |
| 5,164,367 A | 11/1992 | Pickart |
| 5,165,914 A | 11/1992 | Vlock |

| | | | | | |
|---|---|---|---|---|---|
| 5,166,176 A | 11/1992 | Obagi et al. | 5,897,854 A | 4/1999 | Lucas et al. |
| 5,174,990 A | 12/1992 | Douglas | 5,897,855 A | 4/1999 | Trinh et al. |
| 5,177,061 A | 1/1993 | Pickart | 5,897,856 A | 4/1999 | Trinh et al. |
| 5,209,932 A | 5/1993 | Nichols | 5,911,976 A | 6/1999 | Trinh et al. |
| 5,214,032 A | 5/1993 | Pickart | 5,928,631 A | 7/1999 | Lucas et al. |
| 5,227,156 A | 7/1993 | Wiese | 5,928,658 A | 7/1999 | Kishida et al. |
| 5,232,691 A | 8/1993 | Lemole | 5,928,659 A | 7/1999 | Moy |
| 5,240,696 A | 8/1993 | Van Der Ouderaa et al. | 5,935,608 A | 8/1999 | Fujikawa et al. |
| 5,244,651 A | 9/1993 | Kayane et al. | 5,942,214 A | 8/1999 | Lucas et al. |
| 5,258,183 A | 11/1993 | Grimberg | 5,948,390 A | 9/1999 | Nelson et al. |
| 5,310,546 A | 5/1994 | Douglas | 5,951,990 A | 9/1999 | Ptchelintsev |
| 5,330,748 A | 7/1994 | Winston et al. | 5,955,067 A | 9/1999 | Oge et al. |
| 5,330,749 A | 7/1994 | Giacin et al. | 5,961,993 A | 10/1999 | Boussouira et al. |
| 5,348,943 A | 9/1994 | Pickart | 5,965,137 A | 10/1999 | Petrus |
| 5,382,431 A | 1/1995 | Pickart | 5,965,610 A | 10/1999 | Modak et al. |
| 5,385,727 A | 1/1995 | Winston et al. | 5,972,999 A | 10/1999 | Murad |
| 5,401,730 A | 3/1995 | Sauvage et al. | 5,994,403 A | 11/1999 | Donatiello |
| 5,424,077 A | 6/1995 | Lajoie | 6,019,976 A | 2/2000 | Bryant |
| 5,439,863 A | 8/1995 | Bottcher et al. | 6,022,565 A | 2/2000 | Albert et al. |
| 5,455,023 A | 10/1995 | Giacin et al. | 6,030,605 A | 2/2000 | D'Ameila et al. |
| 5,466,470 A | 11/1995 | Lajoie | 6,037,386 A | 3/2000 | Modak et al. |
| 5,480,975 A | 1/1996 | Goldberg et al. | 6,046,178 A | 4/2000 | Silvetti, Sr. |
| 5,482,720 A | 1/1996 | Murphy et al. | 6,060,079 A | 5/2000 | Freeman et al. |
| 5,500,448 A | 3/1996 | Cummins et al. | 6,071,543 A | 6/2000 | Thornfeldt |
| 5,547,676 A | 8/1996 | Rocher et al. | 6,083,490 A | 7/2000 | Ellis et al. |
| 5,550,183 A | 8/1996 | Pickart | 6,086,666 A | 7/2000 | Noguchi et al. |
| 5,552,147 A | 9/1996 | Znaiden et al. | 6,103,247 A | 8/2000 | Boussouira et al. |
| 5,554,375 A | 9/1996 | Pickart | 6,103,273 A | 8/2000 | Antoun |
| 5,554,647 A | 9/1996 | Perricone | 6,113,636 A | 9/2000 | Ogle |
| 5,582,817 A | 12/1996 | Otsu et al. | 6,121,254 A | 9/2000 | Saint-Leger |
| 5,597,550 A | 1/1997 | Mo | 6,123,925 A | 9/2000 | Barry et al. |
| 5,597,552 A | 1/1997 | Herms et al. | 6,132,743 A | 10/2000 | Kuroda et al. |
| 5,616,313 A | 4/1997 | Williams et al. | 6,143,318 A | 11/2000 | Gilchrist et al. |
| 5,622,724 A | 4/1997 | Bryce-Smith | 6,149,947 A | 11/2000 | Hon et al. |
| 5,624,675 A | 4/1997 | Kelly | 6,183,785 B1 | 2/2001 | Westfall |
| 5,631,013 A | 5/1997 | Bergmann et al. | 6,190,407 B1 | 2/2001 | Ogle et al. |
| 5,632,972 A | 5/1997 | Williams et al. | 6,191,167 B1 | 2/2001 | Yu et al. |
| 5,645,840 A | 7/1997 | Lajoie et al. | 6,200,580 B1 | 3/2001 | Horino et al. |
| 5,663,213 A | 9/1997 | Jones et al. | 6,200,680 B1 | 3/2001 | Takeda et al. |
| 5,686,083 A | 11/1997 | Chamness | 6,217,914 B1 | 4/2001 | Meisner |
| 5,688,492 A | 11/1997 | Galley et al. | 6,221,403 B1 | 4/2001 | Nesbit |
| 5,690,967 A | 11/1997 | Yu et al. | 6,224,896 B1 | 5/2001 | Redmond |
| 5,696,169 A | 12/1997 | Otsu et al. | 6,248,370 B1 | 6/2001 | Harris |
| 5,698,184 A | 12/1997 | Pickart | 6,261,574 B1 | 7/2001 | Costello |
| 5,707,609 A | 1/1998 | Mo | 6,267,782 B1 | 7/2001 | Ogle et al. |
| 5,708,023 A | 1/1998 | Modak et al. | 6,287,541 B1 | 9/2001 | Creeth et al. |
| 5,728,404 A | 3/1998 | Von Rheinbaben et al. | 6,303,651 B1 | 10/2001 | Hersh |
| 5,747,005 A | 5/1998 | Barels et al. | 6,322,588 B1 | 11/2001 | Ogle et al. |
| 5,753,637 A | 5/1998 | Fried | 6,322,820 B1 | 11/2001 | Simoneau |
| 5,762,945 A | 6/1998 | Ashley et al. | 6,331,567 B1 | 12/2001 | Watson et al. |
| 5,780,020 A | 7/1998 | Peterson et al. | 6,361,800 B1 | 3/2002 | Cooper et al. |
| 5,795,574 A | 8/1998 | Breton et al. | 6,375,942 B1 | 4/2002 | Rico |
| 5,798,121 A | 8/1998 | Cauwet et al. | 6,395,301 B1 | 5/2002 | Cantin |
| 5,827,884 A | 10/1998 | Obagi et al. | 6,416,744 B1 | 7/2002 | Robinson et al. |
| 5,837,270 A | 11/1998 | Burgess | 6,444,699 B2 | 9/2002 | Meisner |
| 5,855,873 A | 1/1999 | Yam | 6,451,294 B1 | 9/2002 | Simon |
| 5,858,335 A | 1/1999 | Lucas et al. | 6,471,972 B1 | 10/2002 | Bonte et al. |
| 5,858,371 A | 1/1999 | Singh et al. | 6,475,526 B1 | 11/2002 | Smith |
| 5,858,993 A | 1/1999 | Pickart | 6,517,849 B1 | 2/2003 | Seger et al. |
| 5,861,143 A | 1/1999 | Peterson et al. | 6,521,265 B1 | 2/2003 | Patterson |
| 5,861,144 A | 1/1999 | Peterson et al. | 6,558,710 B1 | 5/2003 | Godfrey |
| 5,861,145 A | 1/1999 | Lucas et al. | 6,579,541 B2 | 6/2003 | Antelman |
| 5,861,146 A | 1/1999 | Peterson et al. | 6,582,684 B1 | 6/2003 | Abrahamson |
| 5,861,147 A | 1/1999 | Dodd et al. | 6,582,710 B2 | 6/2003 | Deckers et al. |
| 5,871,718 A | 2/1999 | Lucas et al. | 6,592,852 B1 | 7/2003 | Ryles et al. |
| 5,871,719 A | 2/1999 | Lucas et al. | 6,599,513 B2 | 7/2003 | Deckers et al. |
| 5,874,067 A | 2/1999 | Lucas et al. | 6,607,716 B1 | 8/2003 | Smith et al. |
| 5,874,070 A | 2/1999 | Trinh et al. | 6,627,178 B1 | 9/2003 | Cawthon |
| 5,879,666 A | 3/1999 | Lucas et al. | 6,660,306 B2 | 12/2003 | Peshoff |
| 5,882,638 A | 3/1999 | Dodd et al. | 6,663,852 B2 | 12/2003 | Simon |
| 5,886,184 A | 3/1999 | Dolling et al. | 6,680,073 B1 | 1/2004 | Tarbet |
| 5,888,515 A | 3/1999 | Albert et al. | 6,682,720 B2 | 1/2004 | Ryles et al. |
| 5,888,522 A | 3/1999 | Pickart | 6,696,071 B2 | 2/2004 | Kelly |

| | | |
|---|---|---|
| 6,726,919 B2 | 4/2004 | Pace et al. |
| 6,730,309 B2 | 5/2004 | Horino |
| 6,730,329 B1 | 5/2004 | Smith |
| 6,743,416 B2 | 6/2004 | Riedl |
| 6,750,209 B1 | 6/2004 | Hudson et al. |
| 6,773,698 B1 | 8/2004 | Melinte et al. |
| 6,780,439 B2 | 8/2004 | Wilk |
| 6,800,301 B2 | 10/2004 | Smith |
| 6,833,362 B2 | 12/2004 | Bowen, Jr. et al. |
| 6,844,012 B1 | 1/2005 | Forceville et al. |
| 6,849,277 B2 | 2/2005 | Roig |
| 6,855,341 B2 | 2/2005 | Smith |
| 6,858,201 B2 | 2/2005 | Pickart |
| 6,929,800 B2 | 8/2005 | Salman |
| 6,932,976 B2 | 8/2005 | Brooks |
| 6,939,568 B2 | 9/2005 | Burrell et al. |
| 6,942,878 B2 | 9/2005 | Ishii et al. |
| 6,949,248 B2 | 9/2005 | Nishihama |
| 6,949,249 B2 | 9/2005 | Healy et al. |
| 6,964,782 B1 | 11/2005 | Smith et al. |
| 6,989,156 B2 | 1/2006 | Gillis |
| 7,008,647 B2 | 3/2006 | Burrell et al. |
| 7,014,870 B1 | 3/2006 | Hon et al. |
| 7,049,339 B2 | 5/2006 | Thomson |
| 2001/0014356 A1 | 8/2001 | Yoshida et al. |
| 2001/0041193 A1 | 11/2001 | Meisner |
| 2002/0001629 A1 | 1/2002 | Voellmy |
| 2002/0031557 A1 | 3/2002 | Meisner |
| 2002/0114847 A1* | 8/2002 | Peshoff ............... 424/642 |
| 2002/0182244 A1 | 12/2002 | Jackson |
| 2003/0004564 A1 | 1/2003 | Elkins et al. |
| 2003/0026848 A1 | 2/2003 | Joshi |
| 2003/0035825 A1 | 2/2003 | Shiau et al. |
| 2003/0059484 A1 | 3/2003 | Bonte et al. |
| 2003/0068351 A1 | 4/2003 | Roig |
| 2003/0069369 A1 | 4/2003 | Belenkaya et al. |
| 2003/0072819 A1 | 4/2003 | Tao |
| 2003/0077304 A1 | 4/2003 | McCadden |
| 2003/0077332 A1 | 4/2003 | Godfrey |
| 2003/0082219 A1 | 5/2003 | Warren et al. |
| 2003/0082223 A1 | 5/2003 | Healy et al. |
| 2003/0099721 A1 | 5/2003 | Yoshida et al. |
| 2003/0118623 A1 | 6/2003 | De Paoli Ambrosi |
| 2003/0133991 A1 | 7/2003 | Monroe et al. |
| 2003/0138497 A1 | 7/2003 | Sakuma et al. |
| 2003/0161892 A1 | 8/2003 | McFarland |
| 2003/0190371 A1 | 10/2003 | Graaf et al. |
| 2003/0194446 A1 | 10/2003 | Akes et al. |
| 2003/0199488 A1 | 10/2003 | Trotta |
| 2003/0215412 A1 | 11/2003 | Waugh et al. |
| 2003/0215522 A1 | 11/2003 | Johnson et al. |
| 2003/0224023 A1 | 12/2003 | Faryniarz et al. |
| 2003/0224027 A1 | 12/2003 | Faryniarz et al. |
| 2004/0022863 A1 | 2/2004 | Hamtini |
| 2004/0028708 A1 | 2/2004 | Brooks |
| 2004/0033270 A1 | 2/2004 | Kropf et al. |
| 2004/0037910 A1 | 2/2004 | Hon et al. |
| 2004/0058011 A1 | 3/2004 | Petersson |
| 2004/0058015 A1 | 3/2004 | Tao |
| 2004/0062730 A1 | 4/2004 | Kurosawa et al. |
| 2004/0062817 A1 | 4/2004 | Peshoff |
| 2004/0076686 A1 | 4/2004 | Riesinger |
| 2004/0091551 A1 | 5/2004 | Damji |
| 2004/0101541 A1 | 5/2004 | Heffernan et al. |
| 2004/0109902 A1 | 6/2004 | McDonagh et al. |
| 2004/0131700 A1 | 7/2004 | Cifra et al. |
| 2004/0156875 A1 | 8/2004 | Fabre et al. |
| 2004/0157921 A1 | 8/2004 | Cifra et al. |
| 2004/0170701 A1 | 9/2004 | Carter |
| 2004/0170703 A1 | 9/2004 | Hoekstra et al. |
| 2004/0170712 A1 | 9/2004 | Sadek El Mogy |
| 2004/0175433 A1 | 9/2004 | Thomson |
| 2004/0185015 A1 | 9/2004 | Zhang et al. |
| 2004/0185074 A1 | 9/2004 | Faryniarz et al. |
| 2004/0202689 A1 | 10/2004 | Subramanyan et al. |
| 2004/0220100 A1 | 11/2004 | Waugh et al. |
| 2004/0253321 A1 | 12/2004 | Fechner et al. |
| 2004/0258769 A1 | 12/2004 | Barker et al. |
| 2005/0032751 A1* | 2/2005 | Wang et al. ............. 514/114 |
| 2005/0048010 A1 | 3/2005 | Klis et al. |
| 2005/0069506 A1 | 3/2005 | Katusic et al. |
| 2005/0069588 A1 | 3/2005 | Taal |
| 2005/0074425 A1 | 4/2005 | Waugh et al. |
| 2005/0079229 A1 | 4/2005 | Cawthon |
| 2005/0100571 A1 | 5/2005 | Keyes |
| 2005/0123620 A1 | 6/2005 | Chiou |
| 2005/0136129 A1 | 6/2005 | Verheul-Koot et al. |
| 2005/0175719 A1 | 8/2005 | Sun et al. |
| 2005/0202054 A1 | 9/2005 | Faryniarz et al. |
| 2005/0234239 A1 | 10/2005 | Taillefer et al. |
| 2005/0238730 A1* | 10/2005 | Le Fur et al. ............... 424/642 |
| 2006/0029682 A1 | 2/2006 | Monroe et al. |
| 2006/0036007 A1 | 2/2006 | Hsieh et al. |
| 2007/0163465 A1* | 7/2007 | Anderson et al. ............. 106/12 |

FOREIGN PATENT DOCUMENTS

| | | |
|---|---|---|
| WO | WO 02/10 0383 | 12/2002 |
| WO | WO 2004/039238 A2 | 5/2004 |
| WO | WO 2004/039238 A3 | 5/2004 |
| WO | WO 2006/05 5526 | 5/2006 |
| WO | WO 2007/08 9267 | 8/2007 |

OTHER PUBLICATIONS

Pasán, J., et al., "Malonate-based copper(II) coordination compounds: Ferromagnetic coupling controlled by dicarboxylates", *Polyhedron* 2003, accepted.

Rodríguez-Martín Y., "Alternating cationic-anionic layers in the $[MII(H_2O)_6][Cu^{II}(mal)_2(H_2O)]$ complexes linked through hydrogen bonds (M=Mn, Co, Ni, Cu and Zn; $H_2mal$=Malonic acid)", *CrystEngComm*, 2002, vol. 4, No. 107, 631.

Hernández-Molina M., "A phase transition in the novel three-dimensional compound $[Eu_2(mal)_2(H_2O)_6]$ ($H_2mal$=malonic acid)", *J.Chem.Soc., Dalton Trans.* 2002, vol. 18, 3462.

Rodíguez-Martín, Y., "Structural Versatility of the Malonate Ligand as a Tool for Crystal Engineering in the Design of Molecular Magnets", *Cryst. Eng. Comm.* 2002, vol. 4, No. 87, 522-535.

Rodríguez-Martín, Y., "Combining coordination chemistry and hydrogen bonds: Synthesis, Crystal Structures and thermal behaviour of the complexes $[MII(L)(bpy)(H_2O)_n]\cdot(NO_3)_2$ ($M^{II}$=Cu and Ni, n=1 or 2, L=malonamide, bipy=2,2'-bipyridine)", *J. Coord. Chem.* (2002) *in press.*

Sanchiz, J., "Ferromagnetic coupling in the malonato-bridged copper(II) chains $\{[Cu(Im)_2(mal)]\}_n$ and $\{[Cu(2-MeIm)_2(mal)]\}_n$ ($H_2mal$=Malonic Acid, Im=imidazole and 2-MeIm=2-methylimidazole)", *New J. Chem.* 2002, vol. 26, 1624.

Rodríguez-Martín, Y., "The flexibility of molecular components as a suitable tool in designing extended magnetic systems", *Cryst. Eng. Comm.* 2002, vol. 4, No. 73, 440-446.

Ruiz-Pérez, C., "Dimensionally controlled hydrogen-bonded nanostructures: Synthesis, structure, thermal and magnetic behaviour of the tris-(chelated)nickel(II) complex $[Ni(bipy)_3]Cl_2\cdot 5.5H_2O$ (bipy=2,2'-bipyridine)", *Inorg. Chim. Acta.* 2002, vol. 336, 131-136.

Rodríguez-Martín, Y., "Extended network via hydrogen bond linkages of coordination compounds: Synthesis, crystal structure and thermal behavior of the complexes $[MII(L)_2(NO_3)_2]$ (MII=Cu, Co) and $[Ni(L)_2(H_2O)_2]\cdot(NO_3)_2$ (L=malonamide)", *Inorganica Chimica Acta* . vol. 328, 169-178 (2002).

Rodríguez-Martín, Y., "Synthesis, crystal structure and magnetic properties of $[Cu(bpym)(mal)(H_2O)]\cdot 6H_2O$ and $[Cu_2(bpym)(mal)_2(H_2O)_2]\cdot 4H_2O$ (bpym=2,2'-bipyrimidine, H2mal=Malonic Acid)", *Inorganica Chimica Acta*. vol. 326, 20-26 (2001).

Delgado, F., "Alkali-Templated Malonate Copper (II) Complexes", *Acta Cryst.* A61, C358 (2005).

Naumov, P, et al., "The Crystal Structure of Copper (II) Malonate Trihydrate", *CCACAA*, vol. 75, No. 3, 701-711 (2002).

Filippova I.G., "Polymorphism of Coordination Compounds with Malonic Añid", *Moldavian Journal of the Physical Sciences*, 1vol. 1, No. 3, 87-93 (2002).

Tinker, D. et al., "Role of Selected Nutrients in Synthesis, Accumulation, and Chemical Modification of Connective Tissue Proteins", *Physiolgical Reviews*, vol. 65, No. 3, 607-657 (1985).

Philip, B., et al., "Dietary Zinc & Levels of Collagen, Elastin & Carbohydrate Components of Glycoproteins of Aorta, Skin & Cartilage in Rats", *Indian J. Exp. Biol.*, vol. 16, 370-372 (1978).

Homsy, R. et al., "Characterization of Human Skin Fibroblasts Elastase Activity", *J. Invest. Dermatol*, vol. 91, 472-477 (1988).

International Search Report from International Application No. PCT/US2007/020812 mailed Mar. 5, 2008.

* cited by examiner

METHOD OF WOUND/BURN HEALING USING COPPER-ZINC COMPOSITIONS

CROSS REFERENCE TO RELATED APPLICATION

This Application claims priority benefit of U.S. Provisional Application No. 60/848,616 filed Sep. 28, 2006 the entire disclosure of which is incorporated herein by this reference.

BACKGROUND

1. Technical Field

This disclosure relates to the use of compositions containing copper and zinc active ingredients for pharmaceutical purposes, and more specifically for healing wounds and/or burns.

2. Background of the Invention

The integumentary system includes the skin and all the structures associated with skin such as hair, nails, sweat glands and oil glands. The functions of the integumentary system include, inter alia, providing a protective barrier for the body to prevent the entry of potentially harmful things. Unfortunately, physical trauma to the protective barrier can result in open wounds such as torn, cut or punctured skin, or closed wounds such as contusions. Furthermore, other factors such as disease make some people prone to developing sores and ulcers. For example, diabetes may make some people prone to developing sores and ulcers on portions of the body that have lost sensitivity. Although there are known treatments for alleviating and healing wounds and/or burns, known treatments are problematic in that results vary from patient to patient. Moreover, no one treatment, if ever, obtains maximum benefit for every patient. As a result, some individuals have an increased risk for complications during healing such as bacterial infection. Accordingly, novel skin treatments are continuously sought after to help minimize burns and/or wounds, and decrease healing times thereof.

Accordingly, there remains room for improvement in skin treatment regimens that enhance burn and/or wound healing. What are needed are new skin care compositions and methods for healing burns and/or wounds.

SUMMARY

Active ingredients such as copper-zinc salts of multifunctional organic acids and formulations containing them may be used to treat wounded and/or burned skin. The copper constituent and zinc constituent, which may be cations, may be combined within a single molecule or used individually in separate molecules during topical application to treat wounds or burns. For example, copper and zinc constituents may be topically applied simultaneously to the skin of the user in order to combine the catalytic properties of each constituent. Moreover, the copper and zinc constituents may be topically applied in the same molecule to combine the catalytic properties of each constituent. Accordingly, the combined application of copper and zinc constituents in the same topical treatment provides enhanced wound and/or burn healing biological activity than the use of either constituent alone.

Skin having one or more wounds and/or burns is treated in accordance with the present disclosure by conditioning skin by the topical application of one or more active ingredients to skin. For example, compositions containing copper-zinc malonates can be directly applied to wounded and/or burned skin in need of treatment. Such conditioning by application of copper, zinc, and/or copper-zinc active ingredients may reduce or eliminate wounds and/or burns and make skin look healthier by stimulating collagen and elastin production in the dermis.

In addition, dermatological treatment regimens in accordance with the present disclosure may improve characteristics of a user's wounded or burned skin. The regimens include the repeated topical application of one or more copper-zinc active ingredients. Suitable corrective compositions include, for example, compositions which help to reduce or eliminate burns and/or wounds. In embodiments, compositions including a single molecule having both copper and zinc constituents are applied to wounds and/or burns to increase levels of collagen, elastin, tropoelastin, and/or elastic fibers in the dermis layer. The resulting increase can improve the wound and/or burn and reduce healing time. Thus, suitable corrective compositions include, for example, compositions which help to reduce or eliminate wounds, close wounds, stimulate collagen and elastin production in the dermis, and/or help to reduce or eliminate burns.

These and other aspects of this disclosure will be evident upon reference to the following detailed description.

DETAILED DESCRIPTION OF PREFERRED EMBODIMENTS

Active ingredients are used in accordance with the present disclosure to treat wounds and/or burns. During the wound/burn healing process collagen and elastin are laid down by the body in the wound or burn to give the wound/burn strength and support, allow for expansion and contraction of the tissue, and to help necessary chemical reactions in the tissue. As copper and zinc are biologically needed by the body to catalyze the production of collagen, elastin, tropoelastin and/or elastic fibers in the dermis, active ingredients having copper and/or zinc constituents can be topically applied to the wound and/or burn to promote collagen, elastin, tropoelastin and/or elastic fibers production and treat wounds and/or burns. For example, bimetal complexes having copper and/or zinc constituents can be applied to skin to penetrate the dermis to stimulate production of collagen, elastin, tropoelastin and/or elastic fibers resulting in wound or burn healing.

Suitable active ingredients for use in accordance with the present disclosure include non-toxic compounds containing both copper and zinc. Such copper, zinc, and copper-zinc active ingredients include, but are not limited to, water soluble compounds that contain both copper and zinc. The water-soluble copper-zinc compounds include any copper-zinc salts formed from reacting any multifunctional organic or inorganic acid with any zinc or copper metal and/or their metallic bases. The organic acid can be aromatic or aliphatic. Suitable non-limiting examples of the water-soluble copper-zinc compounds include copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, and combinations thereof. Suitable non-water soluble copper-zinc compounds include any copper-zinc salts found from reacting any multifunctional water insoluble organic acid with zinc or copper metal and/or their metallic bases. Accordingly, suitable non-limiting examples of the non-water soluble copper-zinc compounds include copper-zinc adipate, copper-zinc pimelate, copper-zinc suberate, copper-zinc azealate, copper-zinc sebacate, copper-zinc dodecanoate, and combinations thereof. In embodiments, copper-zinc salts of organic multicarboxylic acids are suitable for use in accordance with the present disclosure.

Accordingly, it is envisioned that multifunctional organic acids such as carboxylic acids may be reacted with any zinc or copper metal and/or their metallic bases to form the active ingredient of the present disclosure. In embodiments, the molar ratio of copper to zinc in the copper-zinc active ingredient is from about 1:1 to about 3:1. In other embodiments, the molar ratio of copper to zinc in the copper-zinc active ingredient is from about 1:1 to about 2:1.

In particular embodiments, non-limiting examples of suitable active ingredients include one or more copper-zinc malonates. As used herein "copper-zinc malonate" refers to any salt substances formed from malonic acid having copper and zinc constituents at various mole ratios of copper and zinc in the same molecule. For example, in embodiments, the molar ratio of copper to zinc in the copper-zinc malonate active ingredient is from about 1:1 to about 3:1. In other embodiments, the molar ratio of copper to zinc in the copper-zinc malonate active ingredient is from about 1:1 to about 2:1. In embodiments, copper-zinc malonate includes about 16.5% copper and about 12.4% zinc. In general, the copper-zinc malonate active ingredients used in accordance with the present disclosure include ingredients that are compounds of copper and zinc with malonic acid. Non-limiting examples of suitable ingredients for the formation of suitable copper-zinc malonates include, but are not limited to, malonic acid, zinc base, copper base, and water.

In forming suitable copper-zinc malonates for use in accordance with the present disclosure, malonic acid is present in amounts that will react with metal cations such as copper and zinc in an aqueous solution. Suitable amounts of malonic acid also include excess amounts in relation to the amount of copper and zinc cations to force reactions. In embodiments, malonic acid is present in a 3:1:1 molar ratio in relation to the copper and zinc constituents. Two or more salts containing copper and zinc constituents can be present in amounts that will react with malonic acid in an aqueous solution. Suitable salts that may be employed in making copper-zinc malonate active ingredients in accordance with this disclosure include metal salts containing complex-forming metal ions of copper and/or zinc. Non-limiting examples of suitable metal basic salts are: copper (I) and (II) salts such as copper carbonate, copper oxide, and copper hydroxide; and zinc salts such as zinc carbonate, zinc oxide, zinc hydroxide, metallic copper and metallic zinc. In embodiments, the reaction media includes two metallic salts, such as cupric carbonate ($CuCO_3 \cdot Cu(OH)_2$), zinc carbonate ($3Zn(OH)_2 \cdot 2ZnCO_3$), or metallic zinc and metallic copper.

In embodiments, any copper salt or zinc salt active ingredient can be topically applied to treat skin. Such conditioning by application of copper or zinc salt active ingredients may reduce or eliminate any wound and/or burn, and stimulate collagen, elastin tropoelastin and/or elastic fiber production in the dermis to facilitate wound closure or burn healing. Suitable non-limiting examples of copper or zinc salts which may be used to treat skin wounds and/or burns include copper (II) malonate and any hydrated form thereof such as copper (II) malonate dihydrate, copper (II) malonate trihydrate, and copper malonate tetrahydrate. Other suitable non-limiting examples of suitable copper or zinc salt active ingredients for treating wounds and/or burns in accordance with the present disclosure include copper or zinc salts of citrate, oxalate, tartarate, malate, succinate, malonate, maleate, aspartate, glutamate, glutarate, fumarate, glucarate, polyacrylic acid, adipate, pimelate, suberate, azealate, sebacate, and/or dodecanoate. Combinations thereof are also possible.

The active ingredient or ingredients may be combined with numerous ingredients to form products to be applied to the skin, or other tissues of humans or other mammals. Such products may include a dermatologically or pharmaceutically acceptable carrier or diluent, vehicle or medium, for example, a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. In embodiments, compositions in accordance with the present disclosure can contain any ingredient conventionally used in cosmetics and/or dermatology.

As an illustrative example, compositions can be formulated to contain active ingredient in amounts from about 0.001 to about 5% by weight of the total composition. In embodiments, products can be formulated to contain active ingredient in an amount from about 0.05 to about 1% by weight of the total composition. In other embodiments, the amount of active ingredient is from about 0.1 to about 0.5% by weight of the total composition. In such embodiments, the copper or zinc salt and/or copper-zinc present may be in a pharmaceutically acceptable salt form.

In embodiments, products containing active ingredients in accordance with the present disclosure can be in the form of solutions, emulsions (including microemulsions), suspensions, creams, fluid cream, oils, lotions, gels, powders, or other typical solid or liquid compositions used for treatment wounded skin. Such compositions may contain, in addition to the copper and/or zinc salts and/or copper-zinc salts in accordance with this disclosure, other ingredients typically used in such products, such as other active cosmetic substances such as retinol, retinol derivatives, allantoin, tocopherol, tocopherol derivatives, niacinamide, phytosterols, isoflavones, panthenol, panthenol derivatives, bisabolol, farnesol, and combinations thereof, other active drug substances such as corticosteroid, metronidazole, sulfacetamide, sulfur, and combinations thereof, antioxidants, antimicrobials, coloring agents, detergents, dyestuffs, emulsifiers, emollients, fillers, fragrances, gelling agents, hydration agents, moisturizers, odor absorbers, natural or synthetic oils, penetration agents, powders, preservatives, solvents, surfactants, thickeners, viscosity-controlling agents, water, distilled water, waxes, and optionally including anesthetics, anti-itch actives, botanical extracts, conditioning agents, darkening or lightening agents, glitter, humectant, mica, minerals, polyphenols, phytomedicinals, silicones or derivatives thereof, skin protectants, sunblocks, vitamins, and mixtures or combinations thereof. Such compositions may also contain, in addition to the copper or zinc salts and/or copper-zinc salts in accordance with this disclosure, one or more: fatty alcohols, fatty acids, organic bases, inorganic bases, wax esters, steroid alcohols, triglyceride esters, phospholipids, polyhydric alcohol esters, fatty alcohol ethers, hydrophilic lanolin derivatives, hydrophilic beeswax derivatives, cocoa butter waxes, silicon oils, pH balancers, cellulose derivatives, hydrocarbon oils, or mixtures and combinations thereof.

In embodiments, product forms can be formulated to contain humectant in amounts from about 1% to about 15% by weight of the total composition. For example glycerine can be added to the composition in amounts from about 1% to about 15% by weight of the total composition. In particular embodiments, glycerine can be added to the composition in amounts from about 1% to about 5% by weight of the total composition.

In embodiments, product forms can be formulated to contain solvent in amounts from about 1% to about 45% by weight of the total composition. For example petroleum derivatives such as propylene glycol can be added to the composition in amounts from about 1% to about 45% by weight of the total composition. In particular embodiments, propylene glycol can be added to the composition in amounts from about 15% to about 30% by weight of the total composition.

In embodiments, product forms can be formulated to contain water in amounts from about 40% to about 99% by weight of the total composition. For example distilled water can be added to the composition in amounts from about 40% to about 99% by weight of the total composition. In particular embodiments, distilled water can be added to the composition in amounts from about 65% to about 80% by weight of the total composition.

The present active ingredients such as copper-zinc active ingredients can be topically applied to skin in need of the reduction or elimination of wounds and/or burns. As used herein the word "treat," "treating" or "treatment" refers to using the compositions of the present disclosure prophylactically to prevent outbreaks of undesirable wounds and/or burns, or therapeutically to ameliorate an existing wound and/or burn. A number of different treatments are now possible, which reduce and/or eliminate wounds and/or burns.

As used herein "wound" or "wounds" refer to any detectable break in the tissues of the body, such as injury to skin. Such injuries can appear due to a number of factors such as, for example, physical trauma such as those caused by external forces such as motor vehicle accidents, falls and the mishandling of sharp objects, tools, machinery and weapons; environmental damage such as sunburns; and/or other diseased or dysfunctional states of the body such as diabetes. Wounds further refers to cuts and scrapes known as open wounds, as well as others, such as deep bruises, or closed wounds. Non-limiting examples of wounds suitable for treatment in accordance with the present disclosure include abrasions such as those caused by scraping to the outer layer of skin; incisions such as those caused by sharp edges, knives, metal edges, broken glass or other sharp object; lacerations or jagged, irregular cuts or tears of the skin; punctures such as those caused by an object piercing the skin layers and creating a small hole; and/or burns. Additional non-limiting wounds suitable for treatment in accordance with the present disclosure include puncture wounds, gaping wounds, wounds having fatty layers, tissue or muscle exposed, wounds having one or more foreign bodies therein, wounds causing severe pain, wounds having blood flowing there from, or any wound that causes numbness or loss of movement below the wound.

Other non-limiting examples of wounds suitable for treatment in accordance with the present disclosure include animal bites, arterial disease, bee stings, bone infections, compromised skin/muscle grafts, gangrene, insect bites, radiation burns, skin tears or lacerations, surgical incisions, including slow or non-healing surgical wounds, post-operation infections, ulcers, including diabetic foot ulcers, pressure ulcers, traumatic ulcers, and venus stasis ulcers, vascular disease such as peripheral or collagenous. It is understood, that the listed wounds are non-limiting and that only a portion of wounds suitable for treatment in accordance with the present disclosure are listed herein.

As used herein "burn" or "burns" refer to any detectable injury to skin caused by energy applied to the skin. The terms further refer to any burning, or charring of the skin, including thermal burns caused by contact with flames, hot liquids, hot surfaces, and other sources of high heat as well as chemical burns and electrical burns. Burn or burns includes first degree burns which may cause skin manifestations such as reddening, pain, and/or mild swelling. One non-limiting example of first degree burn is a sun burn. Burn or burns further refers to second-degree burns involving the first two layers of skin. Signs of second degree burning include, among other things, deep reddening of the skin, blisters, pain, glossy appearance from leaking fluid, and possible skin loss. Burn or burns further refers to third-degree burns which penetrate the entire thickness of the skin and may destroy tissue. Signs of third degree burning include, among other things, loss of skin, dry skin, leathery skin, charred skin having a mottled appearance, and combinations thereof. In some case, skin with a third degree burn may be painless.

Compositions for use in accordance with the present disclosure contain one or more active ingredients capable of contacting skin with copper and zinc in an effective amount to improve a wound and/or condition. As used herein "effective amount" refers to an amount of a compound or composition having copper and zinc constituents in accordance with the present disclosure that is sufficient to induce a particular positive benefit to tissue having a wound and/or burn. The positive benefit can be health-related, or it may be more cosmetic in nature, or it may be a combination of the two. Here, it is believed that the positive benefit is achieved by contacting tissue such as skin with a combination of copper and zinc which can be in the form of copper and zinc ions, and/or one or more salts having copper and zinc constituents, to improve a wound and/or burn condition.

The particular copper-zinc-containing active ingredient or ingredients employed, and the concentration in the compositions, generally depends on the purpose for which the composition is to be applied. For example, the dosage and frequency of application can vary depending upon the type and severity of the wound and/or burn.

Treatments in accordance with the present disclosure contact wounded or burnt skin with one or more active ingredients such as those containing copper and zinc in an effective amount to increase collagen, elastin (insoluble/soluble), elastic fiber and/or tropoelastin levels therein. As used herein "elastin" refers to a protein in the skin that helps maintain resilience and elasticity. Generally, elastin is a protein in connective tissue that is elastic and allows tissues in the body, including skin, to resume their shape after stretching or contracting. For example, when pressure is applied to skin to change its shape, elastin helps skin to return to its original shape. Elastin may be made by linking multiple tropoelastin protein molecules to make a large insoluble cross-linked aggregate. As used herein "tropoelastin" refers to a water-soluble precursor to the elastin molecule, having a molecular weight of about 70000 Daltons. As used herein, "collagen" refers to a fibrous protein that contributes to the physiological functions of connected tissues in the skin, tendon, bones, and cartilage. Generally, the structural unit is tropocollagen composed of 3-polypeptide chains, designated A1, A2, and A3 that form a triple helical structure stabilized by hydrogen bonds. The term collagen further refers to collagen types, such as type I collagen, type II collagen, and type III collagen.

In embodiments, patients are treated by topically applying to a wound/burn in need of collagen, elastin, tropoelastin and/or elastic fibers one or more copper, zinc and/or copper-zinc salts, such as copper-zinc malonate. The active ingredient is applied until the treatment goals are obtained. However, the duration of the treatment can vary depending on the severity of the wound or burn. For example, treatments can last several weeks to months depending on whether the goal of treatment is to promote or repair collagen, elastin, tropoelastin and/or elastic fiber levels in the wounded or burnt skin. In treatment embodiments, 1 to 5 drops of a composition containing 0.1% copper-zinc malonate may be applied to wounded and/or burnt skin twice a day for 4 weeks.

The following non-limiting examples further illustrate methods in accordance with this disclosure.

Example 1

A 65 year old man is suffering from open soars on his feet. A composition containing copper-zinc malonate is applied to the wound twice a day for 10 days. Healing time is reduced.

Example 2

A 25 year old woman is suffering from 6 inch laceration to her right forearm. An emulsion composition suitable for treatment of skin containing an effective amount of copper-zinc malonate active ingredient is applied to her laceration three times a day for 1 week. The application of the copper-zinc malonate active ingredient promotes healing and decreases the time necessary for the wound to close.

Example 3

A 72 year old diabetic woman is suffering from a stage I pressure ulcer characterized by non-blanchable erythema on intact skin. A gel composition suitable for treatment of skin containing an effective amount of copper-zinc malonate active ingredient is routinely applied to the stage I pressure ulcer twice daily. The pressure ulcer is reduced or eliminated.

Example 4

A 72 year old diabetic woman is suffering from a stage II pressure ulcer characterized by partial skin loss involving the epidermis, dermis, or both. The lesion is superficial and presents clinically as a shallow center. A liquid composition suitable for treatment of skin containing an effective amount of copper-zinc malonate active ingredient is applied to the shallow center four times a day for 2 months. The stage II pressure ulcer is reduced or eliminated.

Example 5

A 72 year old diabetic woman is suffering from a stage III pressure ulcer characterized by full thickness skin loss involving damage or necrosis of subcutaneous tissue that extends down to, but not through, underlying fascia. The sore presents clinically as a deep crater. A liquid composition suitable for treatment of skin containing an effective amount of one or more copper-zinc malonate active ingredients is applied to the crater four times a day for 1 month. The stage III pressure ulcer is reduced or eliminated.

Example 6

A 72 year old diabetic woman is suffering from a stage IV pressure ulcer characterized by full thickness skin loss with extensive destruction, and tissue necrosis. A liquid composition suitable for treatment of skin containing an effective amount of copper-zinc malonate active ingredient is applied to the dying tissue four times a day for 1 month. The stage IV pressure ulcer is reduced or eliminated.

Example 7

A 4 year old boy is suffering from a bee sting characterized by pain and swelling. A liquid composition suitable for treatment of skin containing 0.05% copper-zinc malonate active ingredient is applied to the sting four times a day for 2 days. The bee sting is reduced or eliminated.

Example 8

A copper-zinc malonate formulation has the following make-up:

| COMPONENT | % BY WEIGHT |
|---|---|
| Copper-zinc malonate* (Active ingredient) | 0.1% |
| Glycerine | 3.0% |
| Propylene Glycol | 25.0% |
| Distilled Water | 71.9% |

*Copper-zinc malonate was made by mixing 1 mole Zn/1 mole Cu/3 moles malonic acid.

Example 9

A 9 year old boy is suffering from a wound characterized as a 4 inch lesion on his back. The liquid composition of example 8 suitable for treatment of skin containing 0.1% copper-zinc malonate active ingredient is applied to the lesion 4 times a day for 10 days. The lesion is reduced or eliminated.

Example 10

An 18 year old girl with Fitzpatrick skin type II is suffering from a sun burn characterized by red skin on her back. The liquid composition of example 8 suitable for treatment of skin containing 0.1% copper-zinc malonate active ingredient is applied to the sun burn 4 times a day for 4 days. The sun burn is reduced or eliminated.

Example 11

A 36 year old male truck accident victim is suffering from third degree burns on his left wrist and stomach. A liquid composition suitable for treatment of skin containing an effective amount of copper-zinc malonate active ingredient is applied to the third degree burn four times a day for 1 month. The burnt wrist and stomach improve, and healing time is reduced.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of treating a wound or burn comprising topically applying to a wound or burn a composition comprising a copper-zinc active ingredient comprising the reaction product of a polyfunctional carboxylic acid with basic salts of copper and zinc, wherein copper, zinc and the polyfunctional carboxylic acid are in the same molecule.

2. The method as in claim 1 wherein the copper-zinc active ingredient is a water soluble copper-zinc compound.

3. The method as in claim 1 wherein the copper-zinc active ingredient comprises copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

4. The method as in claim 1 wherein the copper-zinc active ingredient is a copper-zinc malonate.

5. The method as in claim 4 wherein the copper-zinc malonate comprises about 16.5% copper and about 12.4% zinc.

6. The method of claim 1 wherein the molar ratio of copper to zinc in the copper-zinc active ingredient is from about 1:1 to about 3:1.

7. The method of claim 1 wherein the molar ratio of copper to zinc in the copper-zinc active ingredient is from about 1:1 to about 2:1.

8. The method of claim 1 wherein the copper-zinc active ingredient is present in an amount from about 0.001 to about 5% by weight of the composition.

9. The method of claim 1 wherein the copper-zinc active ingredient is present in an amount from about 0.05 to about 1% by weight of the composition.

10. The method of claim 1 wherein the copper-zinc active ingredient is present in an amount from about 0.1 to about 0.5% by weight of the composition.

11. The method according to claim 1 wherein an effective amount of copper-zinc malonate composition is applied to the skin of a user to treat skin afflicted with one or more wounds or burns.

12. The method as in claim 11 wherein the wound comprises a laceration, pressure ulcer, burn or combinations thereof.

13. The method as in claim 1 wherein the composition is a solution, emulsion, microemulsion, suspension, cream, lotion, gel, powder, solid composition, or combinations thereof.

14. The method according to claim 1, wherein the composition comprises a dermatologically acceptable carrier or diluent.

15. A method for forming collagen, elastic fibers, elastin, or tropoelastin in the wound or burn of a patient comprising contacting a wound or burn with an effective amount of a composition wherein the composition comprises one or more copper-zinc active ingredients comprising the reaction product of a polyfunctional carboxylic acid with basic salts of copper and zinc, wherein copper, zinc and polyfunctional carboxylic acid are in the same molecule.

16. The method according to claim 15, wherein the composition comprises a dermatologically acceptable carrier or diluent.

17. The method according to claim 15, wherein the copper-zinc active ingredient is a water soluble copper-zinc compound.

18. The method according to claim 15, wherein the copper-zinc active ingredient is selected from the group consisting of copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, and combinations thereof.

19. The method according to claim 15, wherein the copper-zinc active ingredient is a copper-zinc malonate.

20. The method according to claim 19, wherein the copper-zinc malonate comprises about 16.5% copper and about 12.4% zinc.

21. The method according to claim 15, comprising from about 0.001 to about 5 percent by weight of the copper-zinc active ingredient.

22. The method according to claim 15, comprising from about 0.05 to about 1 percent by weight of the copper-zinc active ingredient.

23. The method according to claim 15, comprising from about 0.1 to about 0.5% percent by weight of the copper-zinc active ingredient.

24. The method of claim 15 wherein the composition further comprises a skin lightening agent, a sunscreen agent, a skin conditioning agent, a skin protectant, an emollient, a humectant, or a mixture thereof.

25. A method of treating a wound or burn comprising topically applying to a wound or burn an effective amount of copper-zinc malonate, wherein the molar ratio of copper to zinc in the copper-zinc malonate is from about 1:1 to about 2:1.

26. The method according to claim 25 wherein the copper-zinc malonate was formed in a reaction media including about 1 mole copper from cupric carbonate, about 1 mole of zinc from zinc carbonate and about 3 moles of malonic acid.

* * * * *